(12) United States Patent
Tilse et al.

(10) Patent No.: US 11,565,125 B2
(45) Date of Patent: Jan. 31, 2023

(54) DEVICE FOR DRYING TOOTH OR BONE SURFACES

(71) Applicants: Rainer Tilse, Pforzheim (DE); Tilman Kraus, Pforzheim (DE)

(72) Inventors: Rainer Tilse, Pforzheim (DE); Tilman Kraus, Pforzheim (DE)

( * ) Notice: Subject to any disclaimer, the term of this patent is extended or adjusted under 35 U.S.C. 154(b) by 519 days.

(21) Appl. No.: 16/414,782

(22) Filed: May 17, 2019

(65) Prior Publication Data

US 2019/0269937 A1 Sep. 5, 2019

Related U.S. Application Data

(63) Continuation of application No. PCT/EP2017/080958, filed on Nov. 30, 2017.

(30) Foreign Application Priority Data

Dec. 2, 2016 (CZ) .................... 10 2016 123 345.5

(51) Int. Cl.
| | |
|---|---|
| *A61N 5/06* | (2006.01) |
| *A61B 5/01* | (2006.01) |
| *A61B 5/00* | (2006.01) |
| *A61C 1/00* | (2006.01) |
| *A61F 2/46* | (2006.01) |
| *A61C 1/08* | (2006.01) |
| *A61C 19/04* | (2006.01) |
| *A61C 13/15* | (2006.01) |

(Continued)

(52) U.S. Cl.
CPC .............. *A61N 5/0625* (2013.01); *A61B 5/00* (2013.01); *A61B 5/01* (2013.01); *A61B 5/4547* (2013.01); *A61C 1/0046* (2013.01); *A61C 1/08* (2013.01); *A61C 19/04* (2013.01); *A61F 2/4675* (2013.01); *A61B 5/682* (2013.01); *A61B 2017/00022* (2013.01); *A61B 2017/00084* (2013.01); *A61B 2017/00115* (2013.01); *A61B 2562/029* (2013.01); *A61C 19/003* (2013.01); *A61F 2002/4672* (2013.01); *A61N 5/067* (2021.08); *A61N 2005/0626* (2013.01); *A61N 2005/0659* (2013.01)

(58) Field of Classification Search
CPC .................. A61C 19/04; A61C 1/0046; A61B 2017/00022; A61B 2017/00084; A61B 2017/00115; A61B 5/682; A61B 2562/029; A61N 5/0625; A61N 2005/0626; A61N 2005/0659; A61N 2005/067
USPC ........................................................... 433/27
See application file for complete search history.

(56) References Cited

U.S. PATENT DOCUMENTS

| | | | | |
|---|---|---|---|---|
| 5,228,210 A | * | 7/1993 | Hofmuth | ............. G03D 15/027 34/420 |
| 7,901,400 B2 | | 3/2011 | Wham et al. | |

(Continued)

FOREIGN PATENT DOCUMENTS

| | | |
|---|---|---|
| AU | 2002 355 010 A1 | 6/2004 |
| DE | 100 49 068 A1 | 9/2001 |

(Continued)

*Primary Examiner* — Nicholas D Lucchesi
*Assistant Examiner* — Hao D Mai
(74) *Attorney, Agent, or Firm* — Hackler Daghighian Martino & Novak

(57) ABSTRACT

A device for the drying of tooth or bone surfaces includes a radiation source for irradiating the tooth or bone surface to be dried, a temperature sensor and/or a humidity sensor.

10 Claims, 1 Drawing Sheet

(51) Int. Cl.
  *A61B 17/00* (2006.01)
  *A61N 5/067* (2006.01)

(56) References Cited

U.S. PATENT DOCUMENTS

| | | | | |
|---|---|---|---|---|
| 7,931,645 | B2* | 4/2011 | Strassl | A61C 1/0046 606/13 |
| 8,771,149 | B2* | 7/2014 | Rahman | A61C 19/04 482/8 |
| 9,788,923 | B2 | 10/2017 | Tilse | |
| 2005/0245917 | A1* | 11/2005 | Strassl | A61C 1/0046 606/17 |
| 2006/0166157 | A1* | 7/2006 | Rahman | A61B 5/4833 433/6 |
| 2007/0009856 | A1* | 1/2007 | Jones | A61C 17/20 433/215 |
| 2008/0037018 | A1* | 2/2008 | Hoffmann | A61B 5/0088 356/405 |
| 2011/0183283 | A1* | 7/2011 | Strassl | A61C 1/0046 433/31 |
| 2015/0010878 | A1* | 1/2015 | Seibel | G01J 3/0205 433/27 |
| 2015/0044628 | A1* | 2/2015 | Flyash | A61C 17/20 433/32 |
| 2015/0150479 | A1* | 6/2015 | Yoshino | G01N 33/18 600/547 |
| 2015/0201918 | A1* | 7/2015 | Kumar | A61B 17/1622 606/104 |
| 2015/0230899 | A1 | 8/2015 | Vetter et al. | |
| 2015/0305658 | A1* | 10/2015 | Islam | A61B 5/7257 433/27 |
| 2016/0120615 | A1* | 5/2016 | Scurtescu | A61C 1/0007 433/27 |
| 2016/0135728 | A1* | 5/2016 | Furukawa | A61B 5/6843 600/547 |
| 2017/0173354 | A1* | 6/2017 | Demarest | A61C 19/066 |
| 2018/0218787 | A1* | 8/2018 | Park | A61B 5/0077 |
| 2018/0231475 | A1* | 8/2018 | Brown | A61B 5/05 |
| 2018/0283913 | A1* | 10/2018 | Chen | A61B 5/0008 |

FOREIGN PATENT DOCUMENTS

| | | |
|---|---|---|
| DE | 10 2007 002593 A1 | 7/2008 |
| DE | 10 2012 107 589 A1 | 2/2014 |
| EP | 1 591 076 A2 | 11/2005 |
| JP | 2009268689 A | 11/2009 |
| WO | 00 09030 A1 | 2/2000 |
| WO | 2004 046628 A2 | 6/2004 |
| WO | 2011 006793 A1 | 1/2011 |

* cited by examiner

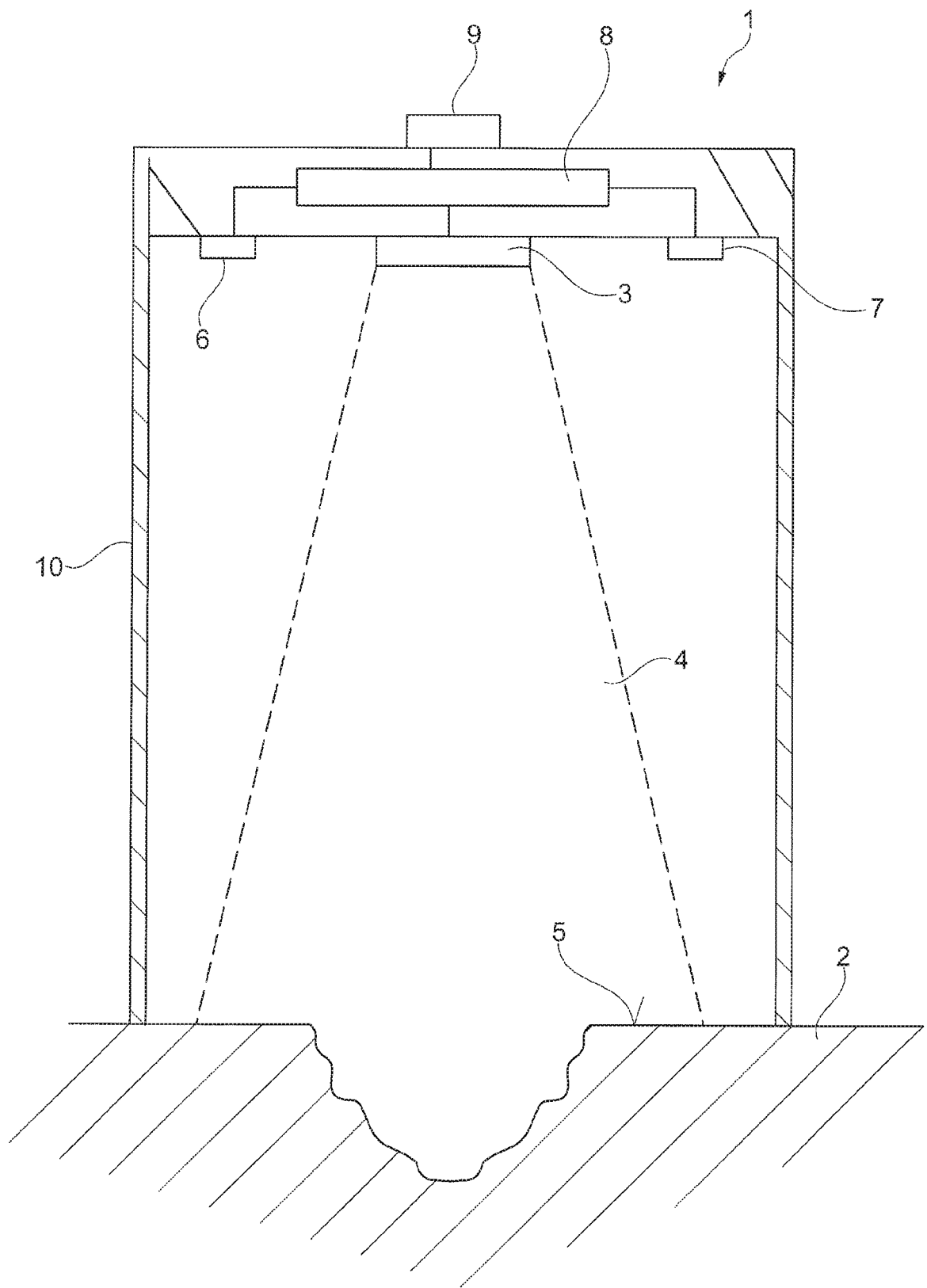

DEVICE FOR DRYING TOOTH OR BONE SURFACES

CROSS-REFERENCE TO RELATED APPLICATIONS

This continuation application claims priority to PCT/EP2017/080958 filed on Nov. 30, 2017 which has published as WO 2018/100056 A1 and also the German application number 10 2016 123 345.5 filed on Dec. 2, 2016, the entire contents of which are fully incorporated herein with these references.

DESCRIPTION

Field of the Invention

The invention relates to a device for the drying of tooth or bone surfaces. From WO 00/09030 A1 it is known to dry tooth surfaces by irradiation with a laser.

Background of the Invention

To treat caries, the affected tooth substance is removed and then replaced with tooth filler material. It is important that the filler material adheres well to the tooth surface formed by the removal of the carious tooth substance. For this to be possible, the tooth surface, which is usually wet, must first be dried. Drying usually takes place by blowing dry air onto the tooth surface or—as mentioned in WO 00/09030 A1—by irradiation.

Similarly, surgical treatment sometimes requires the drying of bone surfaces, for example when inserting artificial joints. Also in such cases a good adhesive bond is to be achieved, namely between the bone on the one hand and the artificial joint on the other hand. For good adhesion, the bone surface cannot be wet, and must therefore be dried.

An object of the present invention is to show a way in which dentists or surgeons can facilitate the drying of tooth or bone surfaces, so that an optimal adhesive bond with the tooth filler material or the bonding agent can be achieved.

SUMMARY OF THE INVENTION

This object is achieved by a device with the features specified in claim 1. Advantageous refinements of the invention are the subject matter of dependent claims.

A device according to the present invention includes a radiation source, such as a laser or diode, to generate radiation for the drying of a tooth or bone surface, together with a temperature sensor to measure the temperature of the tooth or bone surface to be dried, and a moisture sensor. In this way, a tooth or bone surface can be dried by irradiation, and optimum moisture level can be achieved for a given tooth filler material or a given bonding agent. The temperature sensor can be used to prevent excessive heating of the tooth or bone surface, which could lead to damage. The moisture sensor allows you to determine when the moisture level of the tooth or bone surface is within a range that is optimal for forming a good bond to the tooth filler material, or the bone adhesive or cement.

Particularly in the case of plastic-based tooth filler materials, the moisture level of the tooth surface is of critical importance for good adhesion. Too much moisture hinders the formation of a stable chemical bond between the tooth substance and the filler material or adhesion promoter. However, complete drying, that is to say, too little moisture, does not lead to good results either, because collagen fibres contained in the dentin collapse and no longer bond with the filler material or bonding agent. Tooth surfaces that are either too moist or too dry thus lead to a bad adhesive bond. A similar situation occurs in the bonding of artificial joints to bones in surgical applications. Here too the bone surface must not be too moist or too dry for an optimal adhesive bond.

In an advantageous refinement of the invention provision is made for the moisture sensor to measure the air humidity, in particular the air humidity at the tooth or bone surface to be dried. The surface moisture level of the tooth or bone that is critical for the adhesion of tooth filler material or bonding agent correlates strongly with the air humidity, in particular the air humidity close to the tooth or bone surface to be dried. The surface moisture level can therefore be determined from a measurement of the air humidity. The surface moisture level of the tooth or bone surface to be dried can be determined from the measured air humidity by means of empirical data, stored, for example, as tables or curves in a controller of the device. The accuracy of this determination can be increased if the temperature of the tooth or bone surface is also taken into account, that is to say, the surface moisture level is determined from a parametric map as a function of temperature and air humidity.

The humidity sensor can, for example, be a capacitive humidity sensor. Capacitive humidity sensors use a hygroscopic layer as a dielectric, usually made of plastic or ceramic, between the two electrodes of a capacitor. The absorption of moisture into the dielectric changes its properties and consequently the capacitance of the capacitor. The humidity sensor can, for example, also be an impedance sensor or a resistive sensor. Such sensors use a hygroscopic layer between two electrodes, whose electrical resistance changes due to the absorption of moisture.

The humidity sensor can also operate photometrically, for example by measuring the absorption of infrared light from a laser over a defined distance. The absorption of infrared light in air is essentially effected by water, so that the Lambert-Beer law can be used to calculate the air humidity from an absorption measurement.

The temperature sensor can, for example, be a non-contacting measuring thermometer. Radiation thermometers are particularly suitable, which determine the temperature of the tooth or bone surface to be dried on the basis of the heat radiation emitted by the tooth or bone surface.

According to a further advantageous refinement of the invention envisages that the device comprises a spacer to be set in position on a tooth or bone. This ensures that the humidity sensor measures the air humidity near the tooth and bone surface to be dried. In addition, the spacer can shield the air at the tooth or bone surface to be dried from interferences, such as breath. For this purpose the spacer can, for example, be designed as a tube. The humidity sensor can then measure the humidity of the air in the tube largely without interference. The radiation for the drying of the tooth or bone surface then falls through the space surrounded by the tube onto the surface to be dried.

In another advantageous refinement of the invention provision is made for the device to include a controller that evaluates the measuring signals of the temperature sensor and the humidity sensor. The controller can prevent excessive heating of the tooth or bone surface to be dried by controlling the radiation power accordingly. Heating of the tooth or bone surface to more than 42° C. can lead to tissue damage and should therefore be avoided. However, for safety reasons, a lower upper limit for the temperature of the tooth or bone surface can also be set at, for example, 41° C. The controller can regulate the temperature of the tooth or bone surface to a specified setpoint value, for example a value between 39° C. and 42° C.

By evaluating the signals from the temperature sensor and the humidity sensor, the controller can determine when the tooth or bone surface to be dried has an optimum moisture level for the application of tooth filler material, bonding agent or similar, and can then indicate this to a user by means of a signalling unit, for example by means of an optical or acoustic signal. In this way, a signal tone or light can indicate to the user that the drying process has been completed.

Which surface moisture level is optimal for a good adhesive bond can depend on the chemical characteristics of the respective tooth filler material or bonding agent. For a given tooth filler material or bonding agent, however, the optimum moisture level can always be determined, for example, by means of laboratory tests. These can be stored in the controller of the device by the manufacturer for a recommended tooth filler material or a recommended bonding agent. It is also possible for a user to adjust the device to the moisture level that is to be achieved by the drying process.

BRIEF DESCRIPTION OF THE DRAWINGS

Further details and advantages of the invention are explained on an example of embodiment of the invention with reference to the accompanying FIGURE.

FIG. 1 shows a schematic diagram of a device for the drying of tooth or bone surfaces.

DETAILED DESCRIPTION OF THE PREFERRED EMBODIMENTS

FIG. 1 shows a schematic cross-sectional view of a device 1 for the drying of tooth or bone surfaces, together with a tooth 2. The device 1 contains a radiation source 3, for example an infrared laser or a diode. Radiation 4 emitted by the radiation source 3, for example infrared radiation, hits a tooth or bone surface 5 to be dried This causes the tooth or bone to heat up and moisture on the tooth or bone surface 5 to be dried to evaporate.

The device 1 contains a temperature sensor 6 and a humidity sensor 7, which are connected to a controller 8 in the same way as the radiation source 3. The temperature sensor 6 is a non-contacting measuring thermometer and measures the temperature of the tooth or bone surface 5 to be dried, for example, by detecting infrared radiation and determining the surface temperature from the latter. The humidity sensor 7 measures the air humidity and can, for example, be a capacitive or resistive sensor.

The controller 8 evaluates measurement signals from the temperature sensor 6 and the humidity sensor 7 and controls the radiation source 3. The controller 8 prevents the tooth or bone surface 5 from heating up above a specified maximum temperature, e.g. 42° C., in order to prevent damage to the patient's tissue. The controller 8 can regulate the temperature of the tooth and bone surface 5 to a setpoint value, which is between 39° C. and 41° C., for example.

The controller 8 determines the air humidity by evaluating the signals of the humidity sensor 7. From the measured air humidity and the temperature of the tooth and bone surface 5 the surface moisture on the tooth or bone surface 5 can be determined, for example, by means of empirical data which can be stored in the controller 8 as tables, characteristic curves, or parametric maps. As soon as the controller 8 detects a moisture level that allows an optimal bonding in the relevant tooth filler material or bonding agent, the controller 8 automatically terminates the drying process and signals this by actuating the signalling unit 9 connected to the controller 8, which generates an acoustic or optical signal, for example.

The device can have a spacer 10 in the form of a tube so that the measured air humidity is impaired as little as possible by disturbing influences, such as moist breath. The spacer 10 surrounds the radiation cone 4 emitted by the radiation source 3, and the humidity sensor 7, as well as the temperature sensor 6.

LIST OF REFERENCE SYMBOLS

1 Device
2 Tooth
3 Radiation source
4 Radiation cone
5 Tooth or bone surface
6 Temperature sensor
7 Humidity sensor
8 Controller
9 Signalling unit
10 Spacer

What is claimed is:

1. A device for the drying of tooth or bone surfaces, the device comprising:
   a radiation source configured for irradiating the tooth or bone surface to be dried, wherein the radiation source is an infrared laser;
   a temperature sensor;
   a humidity sensor;
   a controller, which controls the radiation source as a function of signals from the temperature sensor and the humidity sensor; and
   a signaling unit connected to the controller, wherein the signaling unit is configured, based on data from the temperature sensor and the humidity sensor, to send an optical and/or acoustic signal being a tone and/or a light indicating to a user when the drying of the tooth has been completed for subsequent application of tooth filler material and/or bonding agent.

2. The device in accordance with claim 1, wherein the humidity sensor is a sensor for determining air humidity.

3. The device in accordance with claim 1, including a spacer configured to be set in position on a tooth or bone, the spacer configured to space the radiation source, the temperature sensor and the humidity sensor a distance apart from the tooth or bone.

4. The device in accordance with claim 3, wherein the spacer is designed as a tube.

5. The device in accordance with claim 1, wherein the controller controls the radiation source such that a predetermined maximum temperature of the tooth or bone surface to be dried is not exceeded.

6. The device in accordance with claim 1, wherein the controller controls the temperature of the tooth or bone surface to be dried to a setpoint value by controlling the radiation source.

7. The device in accordance with claim 1, wherein the temperature sensor is a radiation sensor for non-contacting temperature measurement of the tooth or bone surface to be dried.

8. The device in accordance with claim 1, wherein the signaling unit further generates a second optical and/or acoustic signal as soon as the humidity sensor detects a humidity that reaches or falls below a predetermined threshold value.

9. The device in accordance with claim 1, wherein the device is a tooth or bone surface drying device.

10. A tooth or bone surface drying device, the device comprising:
- a radiation source configured for irradiating the tooth or bone surface to be dried, wherein the radiation source is an infrared laser;
- a temperature sensor;
- a humidity sensor;
- a controller, which controls the radiation source as a function of signals from the temperature sensor and the humidity sensor; and
- a spacer configured to be set in position on a tooth or bone, the spacer configured to space the radiation source, the temperature sensor and the humidity sensor a distance apart from the tooth or bone.

* * * * *